United States Patent [19]

Kivlighn et al.

[11] Patent Number: 5,444,067

[45] Date of Patent: Aug. 22, 1995

[54] PHARMACEUTICAL TREATMENT METHODS USING ANGIOTENSIN II RECEPTOR AGONISTS BEARING A THIOPHENE MOIETY

[75] Inventors: Salah Kivlighn, Blue Bell; Victor J. Lotti, Harleysville, both of Pa.; Ralph A. Rivero, Tinton Falls, N.J.; Peter K. S. Siegl, Blue Bell; Gloria J. Zingaro, Harleysville, both of Pa.

[73] Assignee: Merck & Co., Inc., Rahway, N.J.

[21] Appl. No.: 113,874

[22] Filed: Aug. 30, 1993

[51] Int. Cl.⁶ .......................................... A61K 31/435
[52] U.S. Cl. ...................................... 514/303; 546/118
[58] Field of Search ......................... 546/118; 514/303

[56] References Cited

U.S. PATENT DOCUMENTS 5,177,074  1/1993  Allen et al. ........................ 546/118

OTHER PUBLICATIONS

M. Viswanathan et al., "Enhanced Expression of Angiotensin II at Receptors in the Skin of Rats During Experimental Wound Healing", 1992 FASEB Meeting in Anaheim, Calif., Apr. 5-9, 1992, Abstract No. 447, p. A1013.

B. Kimura et al., "Changes in Angiotensin II (AII) Receptors in Skin During Wound Healing", 1992 FASEB Meeting in Anaheim, Calif., Apr. 5-9, 1992, Abstract No. 448, p. A1013.

*Primary Examiner*—Bernard Dentz
*Attorney, Agent, or Firm*—Valerie J. Camara; Mark R. Daniel; Joseph F. DiPrima

[57] ABSTRACT

This invention relates to compounds represented by formula I:

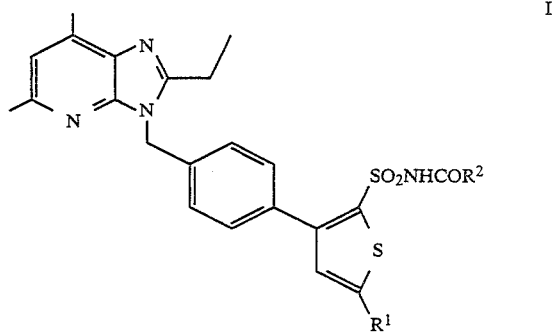

which are agonists of angiotensin II. The invention is also concerned with the use of aforementioned agonists in the treatment of states meditated by angiotensin.

6 Claims, No Drawings

PHARMACEUTICAL TREATMENT METHODS USING ANGIOTENSIN II RECEPTOR AGONISTS BEARING A THIOPHENE MOIETY

SUMMARY OF THE INVENTION

This invention relates to novel compounds of structural formula I which are angiotensin II (AII) agonists that bind to the $AT_1$ and $AT_2$ receptor sites and produce a pharmacologic response. In general, these compounds will be useful in the treatment of any condition in which endogenous production of AII is deficient or the increased effects of AII are considered desirable, although not limited to such conditions.

It also relates to processes for preparing the novel compounds of the invention, their pharmaceutical formulations, and their use as a method of treatment of hypotension and secondary hypoaldosteronism.

BACKGROUND OF THE INVENTION

Renin-angiotensin system (RAS) plays a central role in the regulation of normal blood pressure as well as volume and elecrolyte homeostasis. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS. AII is a powerful arterial vasoconstrictor that exerts its action by interacting with specific receptors present on cell membranes. One of the possible modes of controlling the RAS is angiotensin II receptor antagonism. Several peptide analogs of AII are known to inhibit the effect of this hormone by competitively blocking the receptors, but their experimental and clinical applications have been limited by the partial agonist activity and lack of oral absorption [M. Antonaccio. Clin,. Exp. Hypertens. A4, 27–46 (1982); D. H. P. Streeten and G. H. Anderson, Jr. *Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as AII antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; and 291,969; and in articles by A. T. Chiu, et al. [Eur. J. Pharm. Exp. Therap, 157, 13–21 (1988)] and by P. C. Wong, et al. [J. Pharm, Exp. Therap, 247, 1–7(1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

The pharmocological effects of angiotensin II agonism are generally described in Goodman and Gilman's, "The Pharmlogical Basis of Therapeutics"(8th ed, 1990). Of particular note are sections VI, *Drugs Affecting Renal Function and Electrolyte Metabolism* and sections VII, *Cardiovascular Drugs*.

Imidazo[4,5-b]pyridines beating a thiophene ring are disclosed in U.S. Pat. No. 5,177,074, issued on Jan. 5, 1993 as novel angiotensin II antagonists. The instant application discloses a select group of compounds which are angiotensin II agonists useful in the treatment of hypotension.

DETAILED DESCRIPTION OF THE INVENTION

This invention relates to angiotensin II agonists of structural formula I shown below and which are useful in the treatment of hypotension:

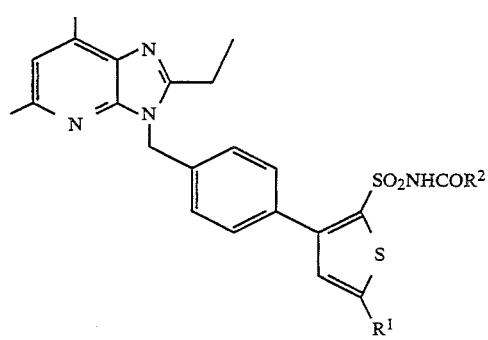

I or a pharmaceutically acceptable salt thereof, wherein:

$R^1$ is: n-butyl or isobutyl; and $R^2$ is: O-n-butyl or $CH_2$-O-n-butyl.

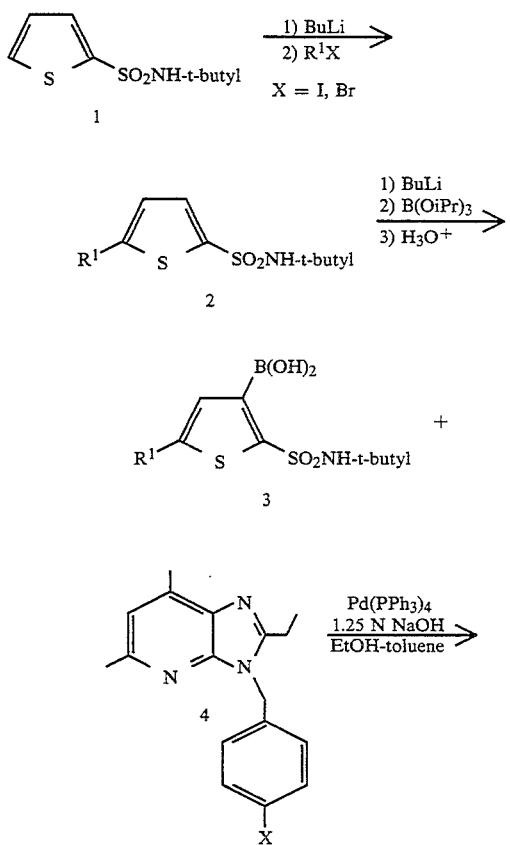

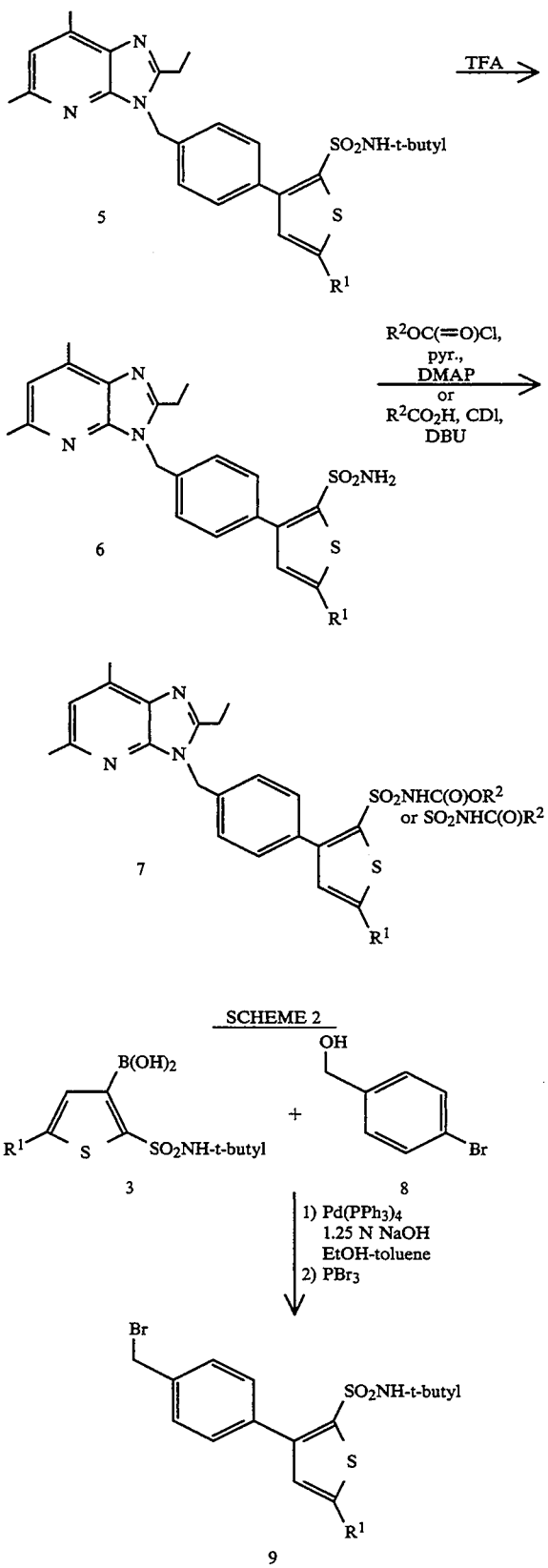

ated with two equivalents of a strong base, such as n-BuLi, is quenched with an appropriate alkyl halide to afford the 5-substituted thiophene, 2. The dianion of 2, generated with two equivalents of a strong base, was quenched with triisopropyl borate to afford, after acid work up, boronic acid derivative 3. Palladium catalyzed coupling of 3 with 4-halo-benzyl imidazopyridine derivative 4 provides the coupled product 5. Deprotection of the sulfonamide with TFA affords 6. Coupling of 6 with a chloroformate in pyridine or an activated acid, prepared with CDI, affords the completed agonists, 7. Alternatively, illustrated in scheme II, the boronic acid derivative 3 can be coupled with 4-bromobenzyl alcohol to provide biaryl 9, after conversion of the alcohol to the bromide with $PBr_3$. Coupling of the benzylbromide with the sodium salt of the imidazopyridine provides 5, which is then further elaborated as described in scheme I.

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, furnaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as agonists of AII at the receptors. In order to identify binding activity and determine their affinity in vitro, the following ligand-receptor binding assays were used along with binding assays reported in the literature (R. S. Chang et al, *Biochem. Biophys. Res, Commun.* 1990, 171, 813.)

Receptor binding assay using rabbit aorta membrane preparation

Three frozen rabbit aorta (obtained from Pel-Freeze Biologicals) were suspended in 5 mM Tris-0.25M Sucrose, pH 7.4 buffer (50 ml) homogenized, and then The synthetic routes used to prepare the angiotensin II agonists of structural formula I are illustrated in schemes I and II. The dianion of sulfonamide 1 genercentrifuged. The mixture was filtered through a cheesecloth and the supernatant was centrifuged for 30 minutes at 20,000 rpm at 4° C. The pellet thus obtained was resuspended in 30 ml of 50 mM Tris-5 mM MgCl$_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 ul; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC$_{50}$) of potential AII antagonist which gives 50% displacement of the total specifically bound $^{125}$I-Sar$^1$Ile$^8$-angiotensin II was presented as a measure of the potency of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [Na$_2$HPO$_4$(10 mM)-NaCl (120 mM)-disodium EDTA (5 mM) containing phenylmethane sulfonyl fluoride (PMSF) (0.1 mM)]. (For screening of compounds, generally duplicates of robes are used). To the membrane preparation (0.5 ml) there was added 3H-angiotensin II (50 mM) (10 ul) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 21560 Tricarb liquid scintillation counter. The inhibitory concentration (IC$_{50}$) of potential AII antagonist which gives 50% displacement of the total specifically bound $^3$H-angiotensin II was presented as a measure of the potency of such compounds as AII antagonists.

Using the methodology described above, representative compounds of this invention were evaluated and were found to exhibit an activity of at least IC$_{50}$<50 μM, thereby demonstrating and confirming the binding of the compounds of the invention to the AII receptors.

The hypertensive effects of the compounds described in the present invention may be evaluated using the methodologies described below:

I: Male Sprague-Dawley rats (200–400 grams body weight) were anesthetized with a short-acting barbiturate (50 mg/kg i.p. methohexital) and instrumented with two chronic vascular catheters the afternoon before the experiment. A catheter in the femoral vein was used for intravenous administration of test compound and test challenges with pressor agents (AII or methoxamine). Rats were permitted to recover overnight from anesthesia and allowed free acces to water. Food was withheld if test compound was administered orally.

Following calibration of pressure transducers and appropriate equilibration, rats were challenged with bolus doses of AII (0.1 μg/kg) and methoxamine (50 μg/kg) to insure patency of catheters and responsiveness of preparation. Rats were then dosed orally or intravenously with the test compound. Blood pressure was continuously monitored throughout the study. Percent inhibition of the pressor responses to AII challenges during the subsequent 6 hours and at 24 hours was used as a measure of AII inhibition. If the test compound increased blood pressure it was considered to be a potential AII agonist and exogenous AII challenges were not administered.

II: Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The fight carotid artery was ligated, both left and right vagal nerves were cut, and the left carotid artery was cannulated with PE 50 robing for drag administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later agonists of formula I were administered intravenously. Blood pressure was then monitored for the duration of the experimental period approximately six hours.

The compounds of the invention are useful in treating hypotension. These compounds may also be expected to be useful in the treatment of hypoaldosteronism, pulmonary hypotension, renal failure, shock, deficiency of antidiuretic hormone, as well as in other conditions in which the maintenance of blood pressure and blood volume would be considered advantageous see Goodman and Gilman: *The Pharmacological Basis of Therapeutics* (sixth edition). Additionally, the compounds of this invention may be useful for enhancing memory and cognition and also for inotropic support of the heart. The application of the compounds of this invention for these and similar disorders will be apparent to those skilled in the art.

In the management of hypotension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 5 to 150 mg. per patient per day.

Typically, the individual daily dosages for these combinations can range from about one-fifth of the minimally recommended clinical dosages to the maximum recommended levels for the entities when they are given singly.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to materials of the above type, a liquid carrier such as fatty oil. Various other materials may be present as coatings or to otherwise modify the physical form of the dosage unit. For instance, tablets may be coated With shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples further illustrate the preparation of the compounds of Formula I and their incorporation into pharmaceutical compositions and, as such, are not to be considered or construed as limiting the invention recited in the appended claims.

EXAMPLE 1

5-butyl-2-(N-t-butylaminosulfonyl)thiophene

To a solution of 2-(N-t-butylaminosulfonyl)thiophene (2.01 g, 9.18 mmol) in anhydrous THF (17 mL) cooled to −78° C. under $N_2$ was added 2.5 M n-BuLi (10 mL, 2.7 equiv). After stirring at −78° C. for 30 min the bath temperature was raised to −40° C. and the mixture was stirred for an additional 2 hrs. To this mixure was added n-butyliodide (2.0 mL, 2 equiv) and the reaction was allowed to warm to room temperature. After stirring overnight the darkened reaction mixture was quenched with $NH_4Cl$ soln and extracted with EtOAc. The organic was washed with brine and dried over anhydrous $MgSO_4$ and concentrated in vacuo. The titled compound was purified by flash chromatography eluting with hex/EtOAc (15:1 to 7:1). Rf=0.32 (6:1 Hex-/EtOAc).

EXAMPLE 2

5-isobutyl-2-(N-t -butylaminosulfonyl)thiophene

The titled compound was prepared using the procedure described for the synthesis of 5-butyl-2-(N-t-butylaminosulfonyl)-thiophene by substituting isobutyliodide for butyliodide. Rf=0.37 (6:1 Hex-/EtOAc).

$^1$H NMR (400 MHz, $CDCl_3$) δ0.92 (d, 6H), 1.26 (s, 9H), 1.86 (m, 1H), 2.66 (d, 2H), 4.58 (s, 1H), 6.65 (d, 1H), 7.40 (d, 1H).

EXAMPLE 3

5,7-dimethyl-2-ethyl-3-[[4-[2-[(butyloxycarbonyl)aminosulfonyl]-5-isobutyl-3-thienyl]phenyl]methyl]imidazo[4,5- b]pyridine Step A; Preparation of 5-isobutyl-2-(N-t-butylaminosulfonyl)-thiophene-3-boric acid To a solution of 5-isobutyl-2-(t-butylsulfonamido)thiophene (1.6 g, 5.82 mmol) in anhydrous THF cooled to −78° C. under $N_2$ was added 2.5M n-BuLi (5.8 mL, 2.5 equiv). The reaction was allowed to warm to −20° C. over a 4 h period. The reaction mixture was stirred for an additional hr at −20° C. To this mixture was added triisopropylborate (2.0 mL, 1.5 equiv). The mixture was warmed to room temperature and stirred overnight. The next day the reaction was quenched with 2N HCl (3 mL) and stirred until the gelatinous solid had dissolved. The mixture was extracted with EtOAc and washed with brine and dried over $MgSO_4$. The organic was concentrated in vacuo to afford the titled product Rf=0.40 (1:1 EtOAc/hex).

Step B: Preparation of 5,7-dimethyl-2-ethyl-3-[[4-[2-(N-t-butylaminosulfonyl)-5-iso-butyl-3-thienyl]phenyl]methyl]-imidazo[4,5-b ]pyridine To a solution of 5,7-dimethyl-2-ethyl-3-[[4-iodophenyl]-methyl]imidazopyridine (948 mg, 2.42 mmol) and the product of step A (1.15 g, 3.61. mmol) in toluene (32 mL) was added 1.25N NaOH (7.5 mL), EtOH (8 mL) and $Pd(PPh_3)_4$ (156 mg, 3 mol %). The reaction mixture was stirred at reflux under $N_2$ for 2 h. After cooling to room temperature the reaction was extracted with EtOAc and washed with 1N NaOH and brine. The organic was dried over anhydrous $MgSO_4$ and concentrated in vacuo. The titled compound was purified by flash chromatography eluting with 1.5:1 hex/EtOAc.
$^1$H NMR (200 MHz, $CD_3OD$) ε0.94 (s, 9H), 0.96 (d, 6H), 1.29 (t, 3H), 1.89 (m, 1H), 2.57 (s, 3H), 2.60 (s, 3H), 2.70 (d, 2H), 2.86 (q, 2H), 5.58 (s, 2H), 6.82 (s, 1H), 7.01 (s, 1H), 7.19 (d, 2H), 7.55 (d, 2H).

Step C: Preparation of 5,7-dimethyl-2-ethyl-3-[[4-[2-(aminosulfonyl)-5-isobutyl-3-thienyl]phenyl]methyl]imidazo[4,5b]pyridine To a mixture of the product of step B (872 mg, 1.62 mmol) and anisole (2 drops) was added TFA (5 mL). After standing at room temperature overnight the reaction was concentrated in vacuo. The residue was dissolved in EtOAc and washed with 2 N $Na_2CO_3$ soln, and brine. The organic was dried over anhydrous $MgSO_4$ and concentrated in vacuo to provide the titled compound, Rf=0.35 (2:1 EtOAc/Hex).

Step D: Preparation of 5,7-dimethyl-2-ethyl-3-[[4-[2-[(butyloxycarbonyl)aminosulfonyl]-5-isobutyl-3-thienyl]phenyl]-methyl]imidazo[4,5-b]pyridine To a solution of the product of step 3 (404 mg, 0.84 mmol) in anhydrous pyridine (3 mL) cooled to 0° C. was added 4-pyrrolidinopyridine (124 mg) and butylchloroformate (1.15 mL, 10 equiv). The next day the reaction was quenched with MeOH and concentrated in vacuo. The residue was dissolved in EtOAc and washed with 10% citric acid, H₂O and brine. The organic was dried over anhydrous MgSO₄ and concentrated in vacuo. The titled compound, Rf=0.56 (40:10:1 CHCl₃/MeOH/NH₄OH), was purified by flash chromatography eluting with 80:10:1 (CHCl₃/MeOH/NH₄OH).

$^1$H NMR (400 MHz, CD₃OD) ∊0.83 (t, 3H), 0.97 (d, 6H), 1.21 (m, 2H), 1.30 (t, 3H), 1.42 (m, 2H), 1.93 (m, 1H), 2.58 (s, 3H), 2.61 (s, 3H), 2.71 (d, 2H), 2.89 (q, 2H), 3.93 (t, 2H), 5.59 (s, 2H), 6.84 (s, 1H), 7.03 (s, 1H), 7.17 (d, 2H), 7.46 (d, 2H).

EXAMPLE 4

5,7-dimethyl-2-ethyl-3-[[4-[2-[(butyloxymethylcarbonyl)aminosulfonyl]-5-isobutyl-3-thienyl]phenyl]methyl]imidazo[4,5-b]pyridine To a solution of butoxyacetic acid (0.028 mL, 0.218 mmol) in dry THF (1 mL) was added CDI (35 mg, 0.22 mmol). After stirring at 50° C. for 2.5 h, a solution of the product of Example 3, step C (35 mg. 0.073 mmol) and DBU (0.033 ml, 0.218 mmol) in THF (1 mL) was added. The reaction mixture was stirred at 50° C. overnight. The next day the reaction was quenched MeOH and the solvent was removed in vacuo. The residue was dissolved in EtOAc and washed with 10% citric acid solution, H₂O and brine. The organic was dried over anhydrous MgSO₄ and concentrated in vacuo. The titled compound, Rf=0.58 (40:10:1 CHCl₃/MeOH/NH₄OH), was purified by flash chromatography eluting with 80:10:1 (CHCl₃/MeOH/NH₄OH).

$^1$H NMR (400 MHz, CD₃OD) ∊0.84 (t, 3H), 0.97 (d, 6H), 1.22 (m, 2H), 1.32 (t, 3H), 1.41 (m, 2H), 1.91 (m, 1H), 2.58 (s, 3H), 2.61 (s, 3H), 2.71 (d, 2H), 2.90 (q, 2H), 3.21 (t, 2H), 3.53 (s, 2H), 5.60 (s, 2H), 6.82 (s, 1H), 7.02 (s, 1H), 7.18 (d, 2H), 7.49 (d, 2H).

EXAMPLE 5

5,7-dimethyl-2-ethyl-3-[[4-[2-[(butyloxycarbonyl)aminosulfonyl]-5-butyl-3-thienyl]phenyl]methyl]imidazo[4.5-b]pyridine

Step A: Preparation of 5-butyl-2-(N-t-butylaminosulfonyl)-thiophene-3-boric acid To a solution of the product of Example 1 (1.52 g, 5.53 mmol) in anhydrous THF (12 mL) cooled to -78° C. under N₂ was added 2.5M n-BuLi (5.53 mL, 2.5 equiv). The reaction was warmed to −40° C. and stirred for 2.5 h. To this mixture was added triisopropyl borate (3.2 mL, 2.5 equiv) and the reaction was allowed to warm to room temperature and stirred overnight. The next day the reaction was quenched with 2N HCl (3 mL) and stirred for 2 h. The solvent was removed and the residue was extracted with EtOAc and washed with H₂O and brine. The organic was dried over anhydrous MgSO₄ and concentrated in vacuo to afford the titled compound. Rf=0.51 (1:1 EtOAc/Hex).

Step B: Preparation of 5-butyl-3-[(4-hydroxymethyl)phenyl]-2-(N-t-butylaminosulfonyl)thiophene To a solution of the product of step A (3.2 g, 9.94 mmol) in toluene (60 mL) and 1N NaOH (17 mL, 2 equiv) was added 4-bromobenzyl alcohol (4.85 g, 3 equiv) in EtOH (15 mL). To this mixture was added Pd(PPh₃)₄ (300 mg, 3 mol%) and the reaction was stirred at reflux for 4 h. The reaction mixture was cooled to room temperature and extracted with EtOAc. The organic was washed with H₂O and brine and dried over anhydrous MgSO₄ and concentrated in vacuo. The titled compound, Rf=0.21 (2:1 Hex/EtOAc), was purified by flash chromatography eluting with 2:1 Hex/EtOAc.

Step C: Preparation of 5-butyl-3-[(4-bromomethyl)phenyl]-2-(t-butylsulfonamido)thiophene To a solution of the product of step B (309 mg, 0.81 mmol) in dry CCl₄ (2 mL) and CH₂Cl₂ (2.5 mL) was added PBr₃ (0.06 mL). After stirring for 30 min the solvent was removed and the reaction mixture was concentrated several times from CCl₄ and CH₂Cl₂. The titled product, Rf=0.56 (2:2 Hex/EtOAc), was purified by flash chromatography eluting with 10:1 Hex/EtOAc.

Step D: Preparation of 5,7-dimethyl-2-ethyl-3-[[4-[2-(N-t-butylaminosulfonyl)-5-butyl-3-thienyl]phenyl]methyl]-imidazo[4,5-b]pyridine To a solution of 5,7-dimethyl-2-ethylimidazo[4,5-b]pyridine (163 mg. 0.93 mmol) in dry DMF (2 mL) was added 60% NaH (41 mg). After stirring at room temperature for 45 min, a solution of the product of step C (276 mg, 0.621 mmol) in DMF (2 mL) was added and the reaction was stirred overnight. The next day the reaction was quenched with sat'd NH₄Cl soln and the DMF was removed in vacuo. The residue was extracted into EtOAc and the organic was washed with H₂O and brine and dried over anhydrous MgSO₄. The titled compound, Rf=0.35 (1:2 Hex/EtOAc), was purified by flash chromatography eluting with 2:1 to 1:2 Hex/EtOAc.

$^1$H NMR (200 MHz, CDCl₃) ∊0.93 (t, 3H), 0.96 (s, 9H), 1.32 (t, 3H), 1.38 (m, 2H), 1.68 (m, 2H), 2.60 (s, 3H), 2.66 (s, 3H), 2.82 (comp m, 4H), 4.02 (s, 1H), 5.52 (s, 2H), 6.72 (s, 1H), 6.94 (s, 1H), 7.22 (d, 2H), 7.53 (d, 2H).

Step E: Preparation of 5,7-dimethyl-2-ethyl-3-[[4-[2-(aminosulfonyl)-5-butyl-3-thienyl]phenyl]methyl]imidazo[4,5-b]pyridine To a mixture of the product of step D (215 mg, 0.40 mmol) and anisole (3 drops) was added TFA (3 mL). After standing at room temperature overnight, the solvent was removed and the residue was dissolved in EtOAc and washed with 2N Na₂CO₃ and brine. The organic was dried over MgSO₄ and concentrated in vacuo to provide the titled compound, Rf=0.31 (20:1 CH₂Cl₂/MeOH).

Step F: Preparation of 5,7-dimethyl-2-ethyl-3-[[4-[2-[(butyloxycarbonyl)aminosulfonyl]- 5-butyl-3 -thienyl]phenyl]methyl]-imidazo[[4,5 -b ]pyridine To a solution of product of step E (26.3 mg, 0.055 mmol) in dry pyridine (0.75 mL) was added a catalytic amount of 4-pyrrolidinopyridine and butylchloroformate (0.07 mL, 10 equiv). After stirring overnight the reaction was quenched with MeOH and the solvent was removed in vacuo. The residue was dissolved in EtOAc and washed with 10% citric acid, H₂O and brine. The organic was dried over MgSO₄ and concentrated in vacuo. The titled compound, Rf= 0.63 (40:10:1

CH$_2$Cl$_2$/MeOH/NH$_4$OH), was purified by flash chromatography eluting with 80:10:1 CH$_2$Cl$_2$/MeOH/NH$_4$OH. $^1$H NMR (400 MHz, CD$_3$OD) ε0.83 (t, 3H), 0.94 (t, 3H), 1.21 (m, 2H), 1.31 (t, 3H), 1.42 (comp m, 4H), 1.68 (m, 2H), 2.57 (s, 3H), 2.60 (s, 3H), 2.82 (t, 2H), 2.86 (q, 2H), 3.87 (t, 2H), 5.58 (s, 2H), 6.81 (s, 1H), 7.02 (s, 1H), 7.14 (d, 2H), 7.50 (d, 2H).

What is claimed is:

1. A method of treating a condition in a mammal, the treatment of which is effected or facilitated by a increase in angiotensin II mediated actions, comprising the administration, in an amount that is effective for agonizing the effect of angiotensin II, of a compound of structural formula I:

I or a pharmaceutically acceptable salt thereof, wherein:
R$^1$ is: n-butyl or isobutyl; and
R$^2$ is: O-n-butyl or CH$_2$-O-n-butyl.

2. The method as recited in claim 1, wherein the compound is selected from the group consisting of:

5,7-dimethyl-2-ethyl-3-[[4-[2-[(butyloxycarbonyl)aminosulfonyl]-5-iso-butyl-3-thienyl]phenyl]methyl]imidazo[4,5-b]pyridine;

5,7-dimethyl-2-ethyl-3-[[4-[2-[(butyloxymethylcarbonyl)aminosulfonyl]-5-iso-butyl-3-thienyl]phenyl]methyl]imidazo[4,5-b]pyridine; or 5,7-dimethyl-2-ethyl-3-[[4-[2-[(butyloxycarbonyl)aminosulfonyl]-5-butyl-3-thienyl]phenyl]methyl]imidazo[4,5-b]pyridine.

3. The method as recited in claim 1, wherein the condition is hypotension.

4. The method as recited in claim 3, wherein the mammal is

5. A method of treatment for cardiovascular disorders selected from the group consisting of: hypotension, hypoaldosteronism, pulmonary hypotension, renal failure, shock, deficiency of antidiuretic hormone, and conditions in which the maintenance of blood pressure and blood volume is considered advantageous by administering to a person in need of such treatment a therapeutically effective amount of a compound of formula I

I or a pharmaceutically acceptable salt thereof, wherein:
R$^1$ is: n-butyl or isobutyl; and
R$^2$ is: O-n-butyl or CH$_2$-O-n-butyl.

6. The method as recited in claim 5 comprising administrating a pharmaceutical composition comprising a therapeutically effective amount of the compound of formula I and a pharmaceutically acceptable carrier.

* * * * *

UNITED STATES PATENT AND TRADEMARK OFFICE
CERTIFICATE OF CORRECTION

PATENT NO. : 5,444,067 (Case Docket No. 18892)

DATED : 8/22/95

INVENTOR(S) : Salah Kivlighn, Victor J. Lotti, Ralph A. Rivero, Peter K.S. Siegl and Gloria J. Zingaro It is certified that error appears in the above-identified patent and that said Letters Patent is hereby corrected as shown below:

At Column 12, Claim 4, beginning at line 9, should read as follows:

4. The method as recited in Claim 3, wherein the mammal is human.

Signed and Sealed this

Twenty-fourth Day of October, 1995

Attest:

BRUCE LEHMAN

*Attesting Officer*    *Commissioner of Patents and Trademarks*